United States Patent [19]

Weiner et al.

[11] Patent Number: 5,049,392

[45] Date of Patent: Sep. 17, 1991

[54] OSMOTICALLY DEPENDENT VESICLES

[75] Inventors: Alan L. Weiner, Lawrenceville; Frank G. Fielder, East Windsor, both of N.J.

[73] Assignee: The Liposome Company, Inc., Princeton, N.J.

[21] Appl. No.: 298,470

[22] Filed: Jan. 18, 1989

[51] Int. Cl.$^5$ .................... A61K 37/22; A61K 39/00; B01J 13/02

[52] U.S. Cl. .................................. 424/450; 436/829; 264/4.1; 264/4.3; 424/88; 514/885

[58] Field of Search .................. 424/450, 1.1; 264/4.1, 264/4.3; 436/829

[56] References Cited

U.S. PATENT DOCUMENTS

| | | | |
|---|---|---|---|
| 4,310,505 | 1/1982 | Baldeschwieler et al. | 424/9 |
| 4,310,506 | 1/1982 | Baldeschwieler et al. | 424/450 |
| 4,376,059 | 3/1983 | Davis et al. | 252/316 |
| 4,478,824 | 10/1984 | Franco et al. | 424/101 |
| 4,522,803 | 6/1985 | Lenk et al. | 424/1.1 |
| 4,588,578 | 5/1986 | Fountain et al. | 424/1.1 |
| 4,721,612 | 1/1988 | Janoff et al. | 424/1.1 |
| 4,776,991 | 10/1988 | Farmer et al. | 264/4.1 |
| 4,844,904 | 7/1989 | Hamaguchi et al. | 424/450 |

FOREIGN PATENT DOCUMENTS

| | | |
|---|---|---|
| WO85/00968 | 3/1985 | World Int. Prop. O. |
| WO86/00238 | 1/1986 | World Int. Prop. O. |
| WO87/00043 | 1/1987 | World Int. Prop. O. |
| WO87/02219 | 4/1987 | World Int. Prop. O. |

OTHER PUBLICATIONS

U.S. patent Ser. No. 225,327; filed 0728/88; Lenk et al.
U.S. patent Ser. No. 079,309; filed 07/29/88; Cullin et al.
U.S. patent Ser. No. 122,613; filed 11/17/87; Bally et al.
U.S. patent Ser. No. 800,545; filed 11/21/85; Cullis et al.
U.S. patent Ser. No. 752,423; filed 07/05/85 Bally et al.
U.S. patent Ser. No. 360,964; filed 06/26/89; Janoff et al.
U.S. patent Ser. No. 284,751; filed 12/12/88; Bally et al.
U.S. patent Ser. No. 759,419; filed 07/26/85; Janoff et al.
U.S. patent Ser. No. 749,161; filed 06/26/85; Bally et al.
U.S. patent Ser. No. 638,809; filed 08/08/84; Janoff et al.
U.S. patent Ser. No. 061,837; filed 06/12/87; Hope et al.
U.S. patent Ser. No. 874,575; filed 06/16/86; Hope et al.
U.S. patent Ser. No. 136,267; filed 12/22/87; Madden.
U.S. patent Ser. No. 164,557; filed 03/07/88; Mayer et al.
U.S. patent Ser. No. 022,154; filed 03/05/87; Mayer et al.
U.S. patent Ser. No. 195,228; filed 05/18/88; Lenk et al.
U.S. patent Ser. No. 053,305; filed 05/22/87; Lenk et al.
Bangham et al., "Diffusion of Univalent Ions Across the Lamellae of Swollen Phospholipids", 1965, J. Mol. Biol. 13:238–252.
Gruner, Liposomes: From Biophysics to Therapeutics, Ostro, Ed., Chapter 1, pp. 1–39 at 11, 23 and 26 (Marcel Dekker, N.Y., 1987).
Merck Index, 10th Ed., pp. misc 47–69 (Merck & Co., 1983).
Papahadjopoulos et al., "Phospholipid Model Membranes I. Structural Characteristics of Hydrated Liquid Crystals", 1968, BBA 135:624–638.
Remington's Pharmaceutical Sciences 16th Ed., pp. 1465–1472 (Mack Publ. Co., Eaton, Pa.).

Primary Examiner—Thurman Page
Assistant Examiner—G. S. Kishore
Attorney, Agent, or Firm—Allen Bloom; Thomas M. Saunders; Ilene L. Janofsky

[57] ABSTRACT

Osmotically derived liposomal vesicles loaded with an active agent are disclosed. Liposomes, including an entrapped osmotic agent, are contacted one or more times with a washing solution which is hypotonic to the entrapped osmotic agent and which contains active agent. The entrapped osmotic agent in the liposome and the active agent in the washing solution are each present in concentrations causing the liposomes to swell, rupture under osmotic pressure, spill osmotic agent into the washing solution and re-form to encapsulate active agent.

11 Claims, 4 Drawing Sheets

OD VESICLES X 64,000
NaCl STEP DILUTION OF EPC MPV'S

OD VESICLES X 64,000
SUCROSE DILUTION BY TANGENTIAL FLOW FILTRATION
OF DMPC/C SPLV'S

OSMOTICALLY DEPENDENT VESICLES

BACKGROUND OF THE INVENTION

The present invention relates to liposomes and, more particularly, to liposome vesicles loaded with an active agent.

Liposomes are man-made microscopic vesicles formed from lipid bilayer membranes containing an entrapped aqueous volume. Liposomes may be unilamellar vesicles (possessing a single bilayer membrane) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic nonpolar tails of the lipid monolayers orient to the center of the bilayer while the hydrophilic head orients toward the aqueous phase.

The original liposome preparation of Bangham, et al. (J. Med. Biol., 1965, 12:238-252) involves suspending phospholipids in an organic solvent which is then evaporated to dryness leaving a phospholipid film on the reaction vessel. Next, an appropriate amount of an aqueous phase is added, the mixture allowed to swell and the resulting liposomes, which consist of multilamellar vesicles (MLVs) are dispersed by mechanical means. This technique provides the basis for the development of the small sonicated unilamellar vesicles described by Papahadjopoulos et al (Biochem. Biophys. Acta., 1968, 135:624-638), and large unilamellar vesicles Unilamellar vesicles may be produced using an extrusion apparatus by a method described in Cullis et al., PCT Application No. WO 87/00238, published Jan. 16, 1986, entitled "Extrusion Technique for Producing Unilamellar Vesicles" incorporated herein by reference. Vesicles made by this technique, called LUVETS, are extruded under pressure through a membrane filter.

Another class of liposomes are those characterized as having substantially equal lamellar solute distribution. This class of liposomes is denominated as stable plurilamellar vesicles (SPLV) as defined in U.S. Pat. No. 4,522,803 to Lenk, et al; monophasic vesicles as described in U.S. Pat. No. 4,558,578 to Fountain, et al. and frozen and thawed multilamellar vesicles (FATMLV) wherein the vesicles are exposed to at least one freeze and thaw cycle; this procedure is described in Bally et al., PCT Publication No. 87/00043, Jan. 15, 1987, entitled "Multilamellar Liposomes Having Improved Trapping Efficiencies" and incorporated herein by reference.

A variety of sterols and their water soluble derivatives have been used to form liposomes; see specifically Janoff et al., U.S. Pat. No. 4,721,612 issued Jan. 26, 1988, entitled "Steroidal Liposomes." Mayhew et al., PCT Publication No. WO 85/00968, published Mar. 14, 1985, described a method for reducing the toxicity of drugs by encapsulating them in liposomes comprising alpha-tocopherol and certain derivatives thereof. Also, a variety of tocopherols and their water soluble derivatives have been used to form liposomes, see Janoff et al., PCT Publication No. WO 87/02219, published Apr. 23, 1987, entitled "Alpha Tocopherol-Based Vesicles."

In the present invention, the term lipid as used herein shall mean any suitable material resulting in a bilayer such that a hydrophobic portion of the lipid material orients toward the interior of the bilayer while a hydrophilic portion orients toward the aqueous phase. Lipids further include highly hydrophobic compounds such as triglycerides, sterols such as cholesterol which can be incorporated into the bilayer. The lipids which can be used in the liposome formulations of the present invention are the phospholipids such as phosphatidylcholine (PC), phosphatidylethanolamine (PE), phosphatidylserine (PS), phosphatidylglycerol (PG), phosphatidic acid (PA), phosphatidylinositol (PI), sphingomyelin (SPM), and the like, alone or in combination. The phospholipids can be synthetic or derived from natural sources such as egg or soy. Useful synthetic phospholipids are dymyristoylphosphatidylcholine (DMPC) and dimyristoylphosphatidylglycerol (DMPG). The liposomes can also contain other steroid components such as polyethylene glycol derivatives of cholesterol (PEG-cholesterols), coprostanol, cholestanol, or cholestane, and combinations of PC and cholesterol. They may also contain organic acid derivatives of sterols such as cholesterol hemisuccinate (CHS), and the like. Organic acid derivatives of tocopherols may also be used as liposome-forming ingredients, such as alpha-tocopherol hemisuccinate (THS). Both CHS- and THS-containing liposomes and their tris salt forms may generally be prepared by any method known in the art for preparing liposomes containing these sterols. In particular, see the procedures of Janoff, et al., U.S. Pat. No. 4,721,612 issued Jan. 26, 1988, entitled "Steroidal Liposomes," and Janoff, et al., PCT Publication No. WO 87/02219, published Apr. 23, 1987, entitled "Alpha-Tocopherol Based Vesicles," filed Sept. 24, 1986, respectively. The liposomes may also contain glycolipids.

As indicated above, liposomes can be employed for delivery of a drug. In a liposome drug delivery system, the pharmaceutically active agent is entrapped during liposome formation and then administered to the patient to be treated. The medicament may be soluble in water or in a non-polar solvent.

A liposome drug delivery system is advantageous in that it affords resistance to rapid clearance of the drug accompanied by a sustained release of the drug which will prolong the drug's action. This, in turn, leads to an increased effectiveness of the drug and allows the use of fewer administrations. In the particular case of vaccines, proteins or other immunogens may be entrapped within or in association with liposomes.

In the dried film MLV technique of Bangham et al described above, hereinafter referred to as the Classical Method), lipids are dissolved in a suitable solvent, the solvent rotoevaporated to form a dry lipid film on the flask and the dry film hydrated with an aqueous medium. Lipophilic drugs are incorporated into the liposome by co-dissolving them in the solvent phase while aqueous soluble materials are entrapped from the hydration buffer. While such technique of drug encapsulation is advantageous in that there are not required disruptive applications of heat, sonication, freezing or the addition of solvents (which can facilitate degradation, denaturation, or inactivation of many drugs, especially proteins), a number of disadvantages do exist. In the first place, the resulting product tends to be unstable both in terms of leakage of drug from the capsule into the external aqueous environment and in terms of the presence of oxidation or lyso products. This instability has been attributed to the uneven distribution of drug in the vesicle. More specifically, it has been found that in the onion-like MLVs, the encapsulated drugs tend to be present in high concentrations in the center of the MLV but at low concentrations at the outer layers of the MLV. This concentration differential creates a state of osmotic non-equilibrium and destabilizes the vesicle. Another problem with MLVs prepared by the Classical Method is that only small amounts of drug are sequestered therein, i.e., only between about 5 and 10% of the drug present in the initial solution. This is highly disadvantageous especially when encapsulating very expensive drugs. Yet another problem with the Classical Method is that the formulation of the films along the walls of the reaction vessel renders it difficult to adapt the process to large scale production techniques.

The stable plurilamellar vesicles (SPLVs) described briefly above and in detail in U.S. Pat. No. 4,522,803 represent a significant improvement as compared to the Classical Method in terms of retention of the pharmaceutically active agent and stability. Thus, unlike the MLVs of the classical method, SPLVs are at osmotic equilibrium by virtue of the homogeneous distribution of solute throughout the concentric aqueous spaces of the liposome.

The monophasic vesicles discussed briefly above (MPVs) and described in detail in U.S. Pat. No. 4,588,578 also have an even dispersion of the pharmaceutically active agent throughout the onion-like vesicle structure and, due to the resulting lack of internal osmotic pressure, are relatively stable. Another significant advantage of MPVs is that they can be prepared without resort to sonication or emulsification operations which can adversely affect the active agent. Finally, it has been observed that MPVs may be at least partially resistant to the harsh physical conditions in the gastrointestinal tract thus making this type of vesicle an excellent candidate for applications requiring such resistance.

As is apparent from the above discussion, the art has made significant improvements to liposomes loaded with an active agent in terms of entrapment efficiencies, stability, adaptability to large scale manufacturing techniques, and use of mild conditions to avoid denaturation or other detrimental effects to the pharmaceutically active agent. However, despite such advances, further improvement in the above-listed properties is sought. For example, most of the present techniques for preparing liposomes loaded with an active agent require the active agent to be contacted with the liposome-forming organic solvent. Where the organic solvent adversely affects the active agent, such as by denaturation where the active agent is a protein, the conventional encapsulation techniques are less suitable. Similar adverse effects can occur during repetitive freeze/thaw procedures or other wash procedures.

SUMMARY OF THE INVENTION

In view of the foregoing, it should be apparent that there still exists a need in the art for a method of producing liposome vesicles loaded with an active agent which does not require contacting such active agent with the organic solvent used to prepare the liposomes yet otherwise gives rise to liposomes which (i) have active agent effectively distributed throughout and thus not unstable due to internal/external osmotic pressure differentials and (ii) have high entrapment efficiencies for the active agent. It is, therefore, a primary objective of the present invention to fulfill that need by providing osmotically derived liposomal vesicles, i.e., liposomes which are loaded with an active agent by osmotic forces in the absence of an organic solvent.

It is a further object of the present invention to provide an osmotic method of producing liposome vesicles loaded with an active agent which does not require process manipulations which will adversely affect the active agent such as temperature changes, ionic charges, pH changes, pressure changes, detergents, chelating agents, or application of energy.

In one embodiment the invention includes a method of producing liposome vesicles comprising active agent comprising contacting liposomes including an entrapped intralamellar osmotic agent (such as a sugar or a salt) one or more times with a washing solution including active agent (such as a drug, dye, or diagnostic agent) wherein said solution is effectively hypotonic to said entrapped osmotic agent. In particular embodiments of the method the active agent is solvent sensitive or process sensitive such as many proteins or immunogens. In some applications contacting of the liposomes with the washing solution is variously accomplished by discrete addition steps, linear osmotic gradient or tangential flow. Usefully the concentration of intralamellar osmotic agent in the intralamellar aqueous phase is from about 50 to about 2,500 mg/ml. Further included is the specific liposome of the method, and particularly wherein the active agent is process sensitive.

In another aspect the invention includes a liposome comprising a process sensitive active agent such as a protein or immunogen.

Additionally the invention comprises a method of producing liposome vesicles loaded with an active agent comprising the steps of:

(i) mixing lipid and osmotic agent in an organic solvent and removing the solvent and suspending the resulting material in an aqueous solution thus forming initial liposomes entrapping the osmotic agent;

(ii) combining the initial liposomes of step (i) with a washing solution of active agent which is effectively hypotonic to the entrapped osmotic agent of the initial liposomes;

the entrapped osmotic agent in the liposome and the washing solution including active agent each being present in relative concentrations such that the washing solution is effectively hypotonic so as to cause the liposomes to swell, rupture under osmotic pressure, release osmotic agent into the washing solution and re-form encapsulating active agent.

In this invention a washing solution is by definition one of tonicity sufficiently hypotonic ("effectively hypotonic") to the entrapped osmotic agent in the liposome that the active agent in the washing solution, including active agent, causes the liposomes to swell, rupture under osmotic pressure, release osmotic agent into said washing solutions and re-form to encapsulate active agent.

Preferably, the liposomes including the osmotic agent are contacted more than one time with washing solution. A washing solution shall be understood to mean an aqueous suspension fluid for liposomes which is effectively hypotonic to the intralamellar osmotic pressure and of sufficient osmotic pressure differential to cause rupture of the lipid bilayers such that aqueous intralamellar space liposomal materials may exit from liposomes and constituents within the washing solution may enter the aqueous intralamellar space. This may be accomplished in discrete addition steps with the washing solution containing the active agent or continuously such as in a tangential flow device.

The osmotic agent is preferably a sugar or a salt capable of producing osmotic pressure across a semi-permeable membrane. Additionally, the inventive process is particularly useful with active agents which are "process sensitive" that is adversely affected by an element of a conventional preparatory process. Examples of such process sensitive active agents are proteins that are denatured by freezing in a freeze thaw process or by the use of a solvent in an organic solvent step.

The method also includes the concentration of intralamellar osmotic agent in the solution being in ranges between about 50 and 2,500 mg/ml as well as wherein the active agent is a protein or immunogen.

With the foregoing and other objects, advantages and features of the invention that will become hereinafter apparent, the nature of the invention may be more clearly understood by reference to the following detailed description of the preferred embodiments, to the appended claims and to the drawings.

DETAILED DESCRIPTION OF THE INVENTION

Figure 1:
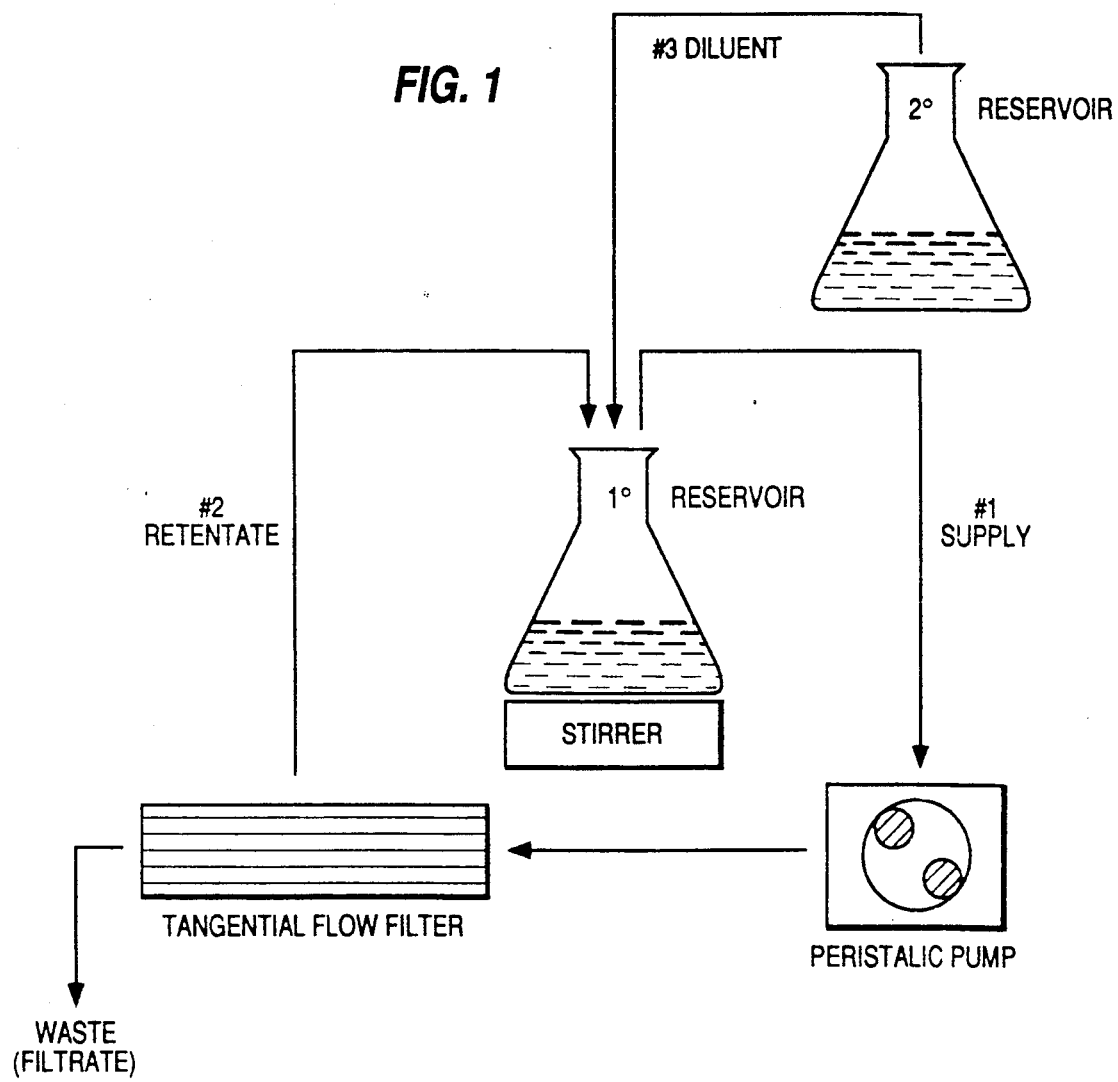
FIG. 1 is a schematic illustration of the large volume dual reservoir system for use with the tangential flow filter.

It has been found that liposomes loaded with an active agent and suitable for therapeutic delivery of a drug may be prepared without the need for contacting the active agent with organic solvents which could adversely affect such active agent. This has been achieved, surprisingly, using osmotic pressure to load the liposome with the active agent.

The preparation of "cell ghosts" has been known for some time. Specifically, cell ghosts, often of erythrocyte origin, are produced by exposing a cell devoid of a cell wall to a hypotonic solution, e.g., distilled water, to cause osmotic influx of the solution into the cell which in turn causes the cell to swell and ultimately to rupture and release the contents of the cell to a surrounding solution. Spontaneous reformation of the membrane yields an empty cell commonly referred to as a ghost. This invention employs a similar process to opposite effect; that is, expelling osmotic agent from vesicles but in the process incorporating exogenous active agents.

According to the present invention, liposomes are produced preferably having concentrations of an osmotic agent such as salts and sugars entrapped therein such that an elevated osmotic pressure or gradient results relative to a washing solution. There is also produced a washing solution, a solution hypotonic to the intralamellar osmotic pressure and of sufficient osmotic pressure differential to cause rupture of the lipid bilayers such that aqueous intralamellar space liposomal materials may exit from liposomes and constituents within the washing solution may enter the aqueous intralamellar space. The tonicity of such a washing solution shall be termed effectively hypotonic. Upon contacting the liposomes with the washing solution the liposomes swell and rupture under osmotic pressure to release osmotic agent into the solution and, ultimately, to re-form whereby an amount of solute is encapsulated. This procedure is advantageously repeated several times to yield additional osmotic agent dispersal as well as additional solute encapsulations. This sequential encapsulation of increasing concentrations of solute can be achieved via discrete step dilutions or by a linear osmotic gradient produced, for example, by tangential flow filtration.

In the present invention, the term lipid as used herein shall mean any suitable material resulting in a bilayer such that a hydrophobic portion of the lipid material orients toward the interior of the bilayer while a hydrophilic portion orients toward the aqueous phase. Lipids further include highly hydrophobic compounds such as triglycerides, sterols such as cholesterol which can be incorporated into the bilayer. The lipids which can be used in the liposome formulations of the present invention are the phospholipids such as phosphatidylcholine (PC), phosphatidylethanolamine (PE), phosphatidylserine (PS), phosphatidylglycerol (PG), phosphatidic acid (PA), phosphatidylinositol (PI), sphingomyelin (SPM), and the like, alone or in combination. The phospholipids can be synthetic or derived from natural sources such as egg or soy. Useful synthetic phospholipids are dymyristoylphosphatidylcholine (DMPC) and dimyristoylphosphatidylglycerol (DMPG). The liposomes can also contain other steroid components such as polyethylene glycol derivatives of cholesterol (PEG-cholesterols), coprostanol, cholestanol, or cholestane, and combinations of PC and cholesterol. They may also contain organic acid derivatives of sterols such as cholesterol hemisuccinate (CHS), and the like. Organic acid derivatives of tocopherols may also be used as liposome-forming ingredients, such as alpha-tocopherol hemisuccinate (THS). Both CHS- and THS-containing liposomes and their tris salt forms may generally be prepared by any method known in the art for preparing liposomes containing these sterols. In particular, see the procedures of Janoff, et al., U.S. Pat. No. 4,721,612 issued Jan. 26, 1988, entitled "Steroidal Liposomes," and Janoff, et al., PCT Publication No. WO 87/02219, published Apr. 23, 1987, entitled "Alpha-Tocopherol Based Vesicles," filed Sept. 24, 1986, respectively. The liposomes may also contain glycolipids.

As previously indicated, an osmotic agent is entrapped within the liposome aqueous intralamellar space. Any of a broad range of osmotic agents are well known to those skilled in the art. Among such agents are sodium chloride and sucrose. Such osmotic agents, which are capable of producing osmotic pressure across a semi-permeable membrane and thus, cause transfer of water into the liposome, are preferably selected from sugars and salts as disclosed in Table 1. Useful osmotic agents are glucose and lactose. The amount of the osmotic agent present in the liposome varies depending on the osmotic agent solubility. Usefully the concentration of intralamellar osmotic agent in the intralamellar aqueous phase is from about 50 to about 2,500 mg/ml. These concentrations are dependent upon the resultant tonicity produced as a function of the osmotic agent itself. For example, an agent such as sucrose produces an isotonic solution at a 9.25% (wt %) concentration while sodium chloride yields equivalent isotonicity at 0.9% (wt %) or a tenfold lower concentration. An extensive listing of the tonicity of various osmotic agents can be found in Remington's Pharmaceutical Sciences 16th Ed. pp 1465-1472 (Mack Publ. Co., Eaton, Pa.) or in the Merck Index, 10th Ed., pp misc 47-69 (Merck & Co., 1983) the teachings of which are incorporated herein by reference. The broadest range of materials may be used as osmotic agents including all of those noted in Remington's or the Merck Index. However limitations such as solubility, toxicity, viscosity and behavior relative to the liposome membrane may restrict the use of a particular osmotic agent or the use in a particular application. In the case of sodium chloride a range between about 5 nd 30 mg/ml is preferred and about 150 to about 250 mg/ml further preferred.

In ideal circumstances, the best osmotic agents are ones which produce the greatest osmotic pressures at lowest concentrations and which are not so viscous at osmotically effective concentrations to inhibit processing of the liposomes. The lower the initial osmotic pressure, the less loading of active agent would be expected. Preferably, the osmotic agents also must not interact adversely with either the lipid or the active agent, as may be the case with high levels of NaCl.

The liposomes having entrapped osmotic agent are prepared by techniques known to persons skilled in the art and described, for example, in U.S. Pat. Nos. 4,522,803 and 4,588,578. Included among such techniques are the monophasic vesicle (MPV) and stable plurilamellar vesicle (SPLV) processes.

Once the liposome loaded with an active agent has been prepared, it is combined with a washing solution which is hypotonic to the entrapped osmotic agent and which contains the active agent. By "hypotonic" is meant a solution having a lower concentration of the solute than the solution entrapped within the liposome—the intralamellar aqueous phase. The washing solution typically is water.

Virtually any active agent (also termed "bioactive agent") can be entrapped within the liposomes for use according to the present invention. However those that are aqueous soluble or can be suspended in an aqueous phase are preferred. Such agents include but are not limited to antibacterial compounds such as gentamicin, antiviral compounds such as rifampacin, antifungal compounds such as candicidin anti-parasitic compounds such as antimony derivatives, antineoplastic compounds such as vinblastine, vincristine, mitomycin C, doxorubicin, daunomycin, methotrextate, and cisplatin, among others, proteins such as albumin, toxins such as diptheria toxin, enzymes such as catalase, hormones such as growth hormone, neurotransmitters such as acetylcholine, lipoproteins such as alpha-lipoprotein, glycoproteins such as hyaluronic acid, immunoglobulins such as IgG, immunomodulators such as the interferons or the interleukins, dyes such as Arsenazo III, radiolabels such as $^{14}C$, radio-opaque compounds such as $^{99}Te$, fluorescent compounds such as carboxy fluoroscein, polysaccharides such as glycogen, cell receptor binding molecules such as estrogen receptor protein, non-steroidal anti-inflammatories such as indomethacin, salicylic acid acetate, ibuprofen, sulindac, piroxicam, and naproxen; antiglaucomic agents such as timolol or pilocarpine, anesthetics such as dibucaine, nucleic acids such as thymine, polynucleotides such as RNA polymers Also included are various bioactive chemical entities such as peptides, hormones, toxins, enzymes, neurotransmitters, lipoproteins, glycoproteins, immunomodulators, immunoglobulins, polysaccharides, cell receptor binding molecules, nucleic acids, polynucleotides, and the like, as well as biological tracer substances such as dyes, radio-opaque agents, and fluorescent agents. In the utilization of more lipophilic agents it may be desireable to convert the agent to a soluble form such as a soluble salt.

The active agent is dissolved or suspended or otherwise mobilized in aqueous solution in an amount high enough to ultimately give rise to encapsulation of substantial amounts of the active agent in the liposome but not so high as to cause the osmolarity of the washing solution to be higher than the osmolarity of the aqueous intralamellar space in the liposome. The maximum amount of active agent present in the washing solution will vary depending upon the solubility or dispersability of the active agent and the relative intralamellar to washing solution osmotic differential as well as the tensile strength of the liposomes.

Upon exposure to the washing solution, the liposomes swell and rupture under osmotic pressure thereby releasing osmotic agent into the solution and re-forming to encapsulate the active agent. The amount of osmotic differential necessary to establish the effectively hypotonic solution to practice this invention will vary with the osmotic agent and the relative osmotic properties of the lipids, media in which the liposomes are suspended, and other factors well known to those skilled in the art.

The particular effective osmotic concentration is easily determined by empirical observation. The tensile limits of the liposome bilayers can be empirically determined by any number of methods. For example, the liposome of interest can be formed encapsulating the desired osmotic agent in a range of concentrations along with a detectable amount of aqueous soluble marker agent. Useful marker agents include radioisotopes, fluorescent materials and dyes. The preferred marker agents are those easily detectable by common techniques such as scintillation counting, fluorescent spectroscopy or colorometric spectroscopy but other markers and detection methods are acceptable. Upon exposure of such liposomes to the external hypotonic solution the presence of marker agent in such solution will indicate the fact of liposome rupture and indicate degree of rupture. In some instances it will be desirable to centrifuge or otherwise separate the liposome challenged by the hypotonic solution to separate the liposomes from the suspending medium and thus quantify those liposomes that have ruptured to disgorge marker agent and re-formed as liposomes. In the practice of this invention, liposomes may release only a portion of the contents on rupture and then reform to a continent state.

Liposomes formed with amounts of osmotic agent insufficient to rupture the liposomes generally will not release marker agent into suspending solution. Empirical observation will thus easily determine an effective concentration of osmotic agent in spite of variables such as rigidity of the lipids used, the different strengths of bilayers of larger spheres as compared to smaller spheres, composition of the buffer in which the liposomes are suspended.

To calculate the osmolarity required for rupture reference is made to analysis of the pertinent physical forces. The physical forces entailed in osmotic liposome rupture—elastic moduli and tensile limits—are detailed a discussion by Gruner, S., "Materials Properties of Liposomal Bilayers" is found in *Liposomes: From Biophysics to Therapeutics*, Ostro, M., Ed., pp1-39 at 11, 23 and 26 (Marcel Dekker, New York 1987) incorporated herein by reference.

In a preferred embodiment of the invention, the osmotic process is repeated to rupture a plurality of times, e.g., in discrete addition steps, in order to effect loading of progressively higher concentrations of active agent into the liposome. Thus, the repeated use of internal/external osmotic pressure differential in a batch-wise addition of washing solution or solutions causes repeated liposome rupture and is followed by liposome reformation and sequential increases in capture of active agent. However, unlike repetitive freeze/thaw techniques, the repetitive osmotic technique of the present invention does not adversely affect active agents which are process sensitive.

The above described sequential incremental increases in the concentration of active agent within the liposome according to the present invention can be achieved via various processes including discrete step dilutions and a linear osmotic gradient produced by tangential flow filtration, followed by terminal sterilization of the vesicles.

In tangential flow filtration, a stack of filters is provided having a pore size such that liposomes and active agents are excluded by the filter but solvent and free osmotic agent can pass through. Liposomes containing osmotic agent and active agent in diluent are loaded onto the retentate side of the filter unit. A plurality of unit volumes of diluent is then passed through the tangential flow unit (one unit volume=initial volume of lipid: active agent: osmotic agent)causing the rupture of liposomes which then reform and concomitantly incorporate active agent The filter unit is flushed of the reformed liposomes and free active agent using additional diluent. The initial filters are then replaced with filters having a pore size great enough to allow passage of the free active agent but not the liposomes. Diluent is again passed through to allow the filtration off of free active agent. Finally, liposomal vesicles loaded with the active agent are flushed from the filter unit with diluent and can be further centrifuged to separate any residual free active agent in solution and concentrate vesicles prior to assaying, e.g., at about 10,000 rpm for about 15 minutes. Tangential flow filtration is more fully discussed in U.S. patent application Ser. No. 225,327 filed Jul. 28, 1988 and incorporated here in by reference.

It will be appreciated that the tangential flow device described above is highly versatile for use in contacting the liposomes loaded with osmotic agent with the solution of active agent since a wide range of filter pore sizes (allowing loading of agents within a range of molecular weights through the use of different molecular weight cutoff filter combinations) are available. It is further noted that tangential flow filtration is an effective means for restricting vesicle sizes in liposome preparations for parenteral administration. Thus, by varying filter combinations and configurations in the tangential flow unit, it is possible to manipulate final vesicle size distributions in order to meet specific particle size requirements.

The above-described process is adaptable to scaling up. More specifically, by selecting an appropriate configuration of the tangential flow filtration units and pumps, it is possible to carry out of the process in a flow-type production cycle as opposed to the batch-type production scheme employed in the classical dried-film liposome manufacturing technique.

The liposomes including a pharmaceutically active agent can be administered alone or in admixture with an acceptable pharmaceutical carrier chosen according to the intended route of administration and standard pharmaceutical practices. The preparations may be injected parenterally, for example, intra-arterially or intravenously. The preparation may also be administered via oral, subcutaneous or intramuscular routes, or by inhalation. For parenteral administration, they can be used, for example, in the form of a sterile aqueous solution which may contain other solutes, for example, enough salts or glucose to make the solution isotonic. Other uses, depending upon the particular properties of the preparation, may be envisioned by those skilled in the art.

The following examples are given by way of illustration and in no way should be construed as limiting with respect to the subject matter disclosed and claimed.

EXAMPLE 1

Salt Osmotic Agent Vesicles

A preparation of liposomes (egg PC, research grade—97% pure) containing sodium chloride as the osmotic agent was made using methylene chloride resulting in production of a stable plurilamellar vesicle (SPLV) process as described in U.S. Pat. No. 4,522,803. 1 gm egg PC and 20 mg methylene chloride are added to 3.33 ml of 22.8% (w/v) sodium chloride in water. The preparation was mixed with a stir paddle set-up in a triple necked 500 ml roundbottom flask to keep the immiscible methylene chloride and sodium chloride-water in a continuous emulsion phase Upon complete removal of methylene chloride under reduced pressure and elevated temperature the lipid drug residue was resuspended in 1 ml water containing $^{14}C$ labeled-inulin of known activity This preparation was vortexed vigorously for 5 minutes or until total dispersion of the initial product had occurred A 100 ul aliquot of the preparation was sampled for scintillation counting and the total volume was determined prior to centrifugation. The preparation was centrifuged at 10,000 rpm for 10 min. and the supernatant was removed. A 100 ul aliquot of supernatant was sampled for scintillation counting with total volume determined for later calculations. A 1:1 (v:v) addition of aqueous $^{14}C$-inulin standard was performed on the remaining pellet with subsequent vortexing and centrifugation. Three repetitions of the addition centrifugation step dilutions were performed, with sampling of supernatants for scintillation counting occurring after each repetition and on the final pellet. The 100 ul aliquots were counted on a Beckman LS6800 scintillation counter to determine dpm's for the initial hydrated preparation, all supernatants and the final pellet. Entrapment of 14C-inulin was determined by the percent of disintegrations per minute (dpm's) in the final pellet as calculated against the total dpm's from all supernatants and the final pellet combined, with a total recovery comparison against the combined activity of all aqueous $^{14}C$-inulin standard additions.

The percent loading of $^{14}C$-inulin in the NaCl step dilution procedure and BSA is given in Table 2.

EXAMPLE 2

Sugar Osmotic Agent Vesicles

A tangential flow filtration unit was used for osmotically derived vesicle production in preparations where a sugar (glucose, lactose, mannitol or sucrose) was employed as the osmotic agent. Bovine serum albumin (BSA) was used specifically for entrapment determinations as a representative example for the entrapment of solvent sensitive compounds. Liposome preparations for tangential flow filtration were made by a modified SPLV process as described in Gruner, S., "Materials properties of Liposomal Bilayers" is found in *Liposomes: From Biophysics to Therapeutics,* Ostro, M., Ed., pp.1-39 at 11, 23 and 26 (Marcel Dekker, New York 1987). In the modified SPLV process, applicable only to small volume preparations (less than 50 mls), biphasic aqueous (sugar) and solvent (lipid) systems were mixed by turning in a 500 ml roundbottom flask at high rpm on a rotoevaporator, yielding an emulsion of the immiscible aqueous and organic phases. Application of vacuum then results in solvent removal and liposome formation. Either L-alpha-dimyristoyl phosphatidylcholine (DMPG)/Cholesterol (7:3 molar ratio) DMPC alone or egg PC liposomes were made employing this process with methylene chloride as the organic solvent. Aqueous phases consisted of one of the above sugars, generally in saturated solution Resulting liposomes were hydrated in the same aqueous phase as that used for liposome production, with the addition of BSA to the hydrating solution after rehydration had occurred to place BSA for entrapment in free solution prior to formation of the osmotically derived vesicles.

In the large volume dual reservoir system (see FIG. 1), a tangential flow filtration unit was set up so that a primary reservoir contained liposome:BSA:sugar solution. A 500 ml Ehrlenmyer flask and a three-holed stopper with three glass tubes was employed, creating a closed system. Of the three tubes, #1 was the supply for the tangential flow filtration unit via a peristaltic pump, #2 returned retentate from the filters to the primary reservoir, and #3 supplied distilled water as diluent from a secondary reservoir. By operating the filter system and removing filtrate to a waste container, the primary reservoir was at negative pressure resulting in the constant addition of diluent to the system from the secondary reservoir. The primary reservoir was continuously mixed by a magnetic stirrer and stir plate during the process to provide even distribution of diluent into the recycling retentate.

The filtration process began with a 10,000 MW cutoff filter which allowed removal of the sugar from liposome rupture in diluent, with retention of both liposomes and BSA, MW approx. 68,000. After 10 unit volumes (initial volume of lipid:BSA;sugar=1 unit volume) of diluent had been passed through the system as filtrate, the filter unit was flushed of lipid:BSA with diluent and 300,000 MW filters replaced the 10,000 MW filters. The lipid:BSA preparation was again filtered with 10 unit volumes of diluent, the 300,000 MW cutoff permitting the removal of free BSA with subsequent retention of liposomal BSA in osmotic derived ("OD") vesicles of this invention. OD vesicles were flushed from the filter unit with diluent and centrifuged at 10,000 rpm for 15 minutes to separate any residual free BSA in solution and concentrate vesicles prior to assay for protein content.

Figure 2:
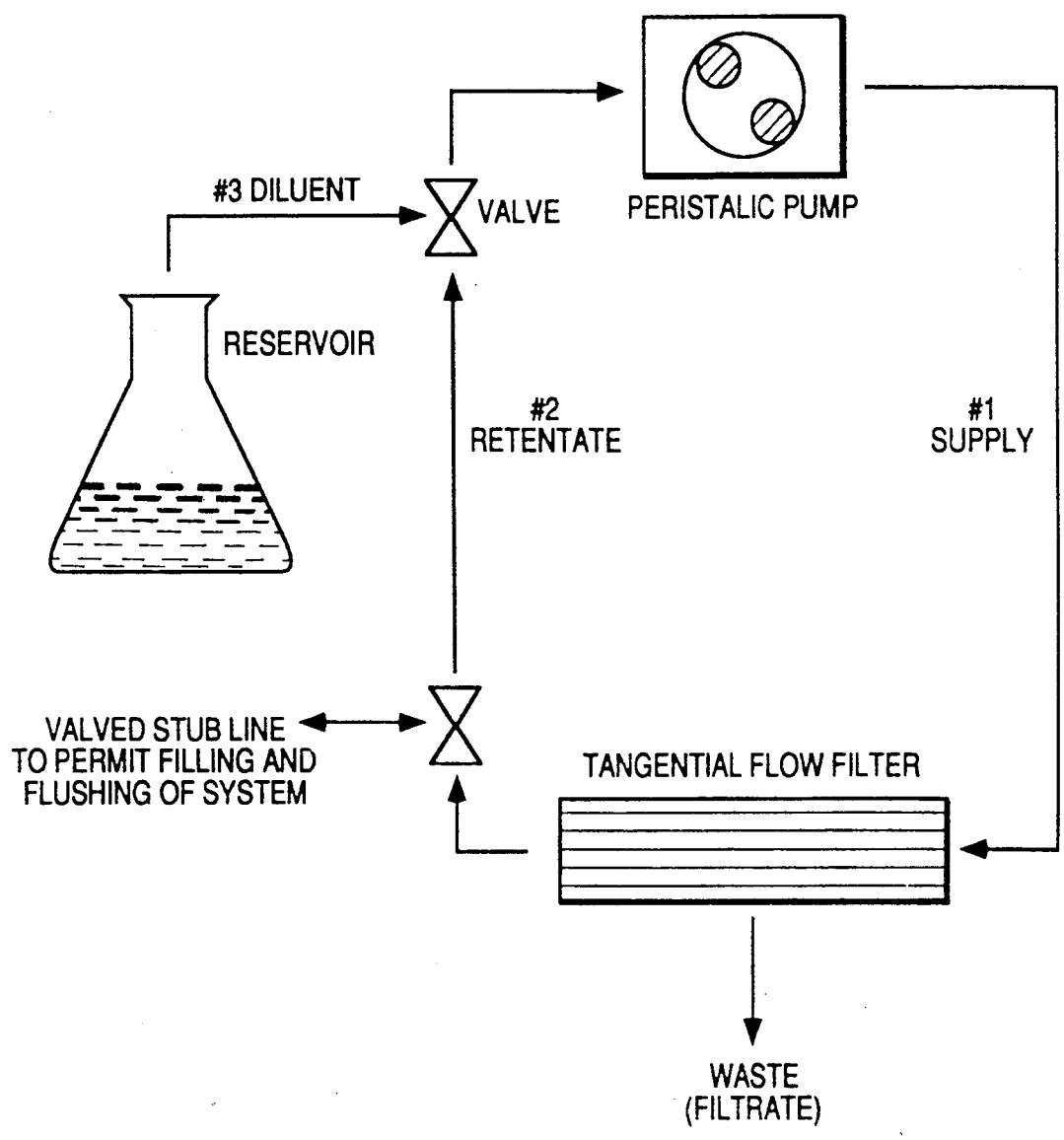
FIG. 2 is a schematic illustration of the small volume single reservoir system for use with the tangential flow filter.

As illustrated in FIG. 2, a small volume single reservoir system was set up to minimize volume in the tangential flow filtration process. Elimination of the primary reservoir allowed the fitting of the retentate line (#2) directly to the peristatic pump with immediate return to the supply line (#1) and the tangential flow filter unit. The retentate line was fitted with two T valves, the first as a connector for diluent supply (#3) and the second as a stub line to permit loading and flushing of the system. All other process parameters remained the same, as previously described.

To assay osmotically derived vesicles for BSA loading the protein was extracted from the vesicles. The extraction was performed by placing 1 ml of the concentrated vesicles in a 30 ml Corex tube and adding 24 mls of chloroform:ethanol (1:1, v:v) to solubilize the lipid and precipitate entrapped BSA. The sample was centrifuged at 10,000 rpm for 30 minutes and the supernatant removed to a 250 ml tared roundbottom flask. The pelleted protein was washed with another 24 ml of chloroform:ethanol (1:1) and centrifuged for 30 minutes at 10,000 rpm to remove any residual lipid. The supernatant was combined with the previous supernatant in the tared roundbottom flask and rotoevaporated to dryness. The roundbottom flask was then re-weighed to determine total lipid.

The pelleted protein was dried in a sample dryer under a nitrogen stream and resolubilized in 1 ml of 1% Triton X-100 TM (octylphenoxypolyethoxyethanol, Rhom & Haas Co., Philadelphia, Pa.). Protein concentration in this sample was determined by the Pierce BCA protein assay (Rockford, Ill.) using the room temperature protocol given in the instruction manual. Standards were set up according to the Pierce protocol for standards to be used with the room temperature assay, except that BSA was solubilized in 1% Triton X-100 TM. Samples were serially diluted to the following degrees: neat (no dilution), 2 times, 5 times, 10 times, 20 times, 50 times, 100 times, 200 times 500 times and 1000 times. One hundred microliter aliquots of standards and samples were treated as per instructions and assay values determined using polystyrene microcuvettes in a Shimadzu UV-160 recording spectrophotometer at 562 nm. The concentration of the original sample was determined by extrapolating back from dilution concentrations which fell within the range delineated by the BSA standards and averaging those values. The BSA concentration in mg/ml was then calculated as a percentage of the lipid concentration in mg/ml to yield protein loading values for the OD vesicle process. The results are shown in Table 2.

Figure 3:
FIG. 3 is a freeze-fracture replicate of EPC:sodium chloride:14C inulin vesicles.
Figure 4:
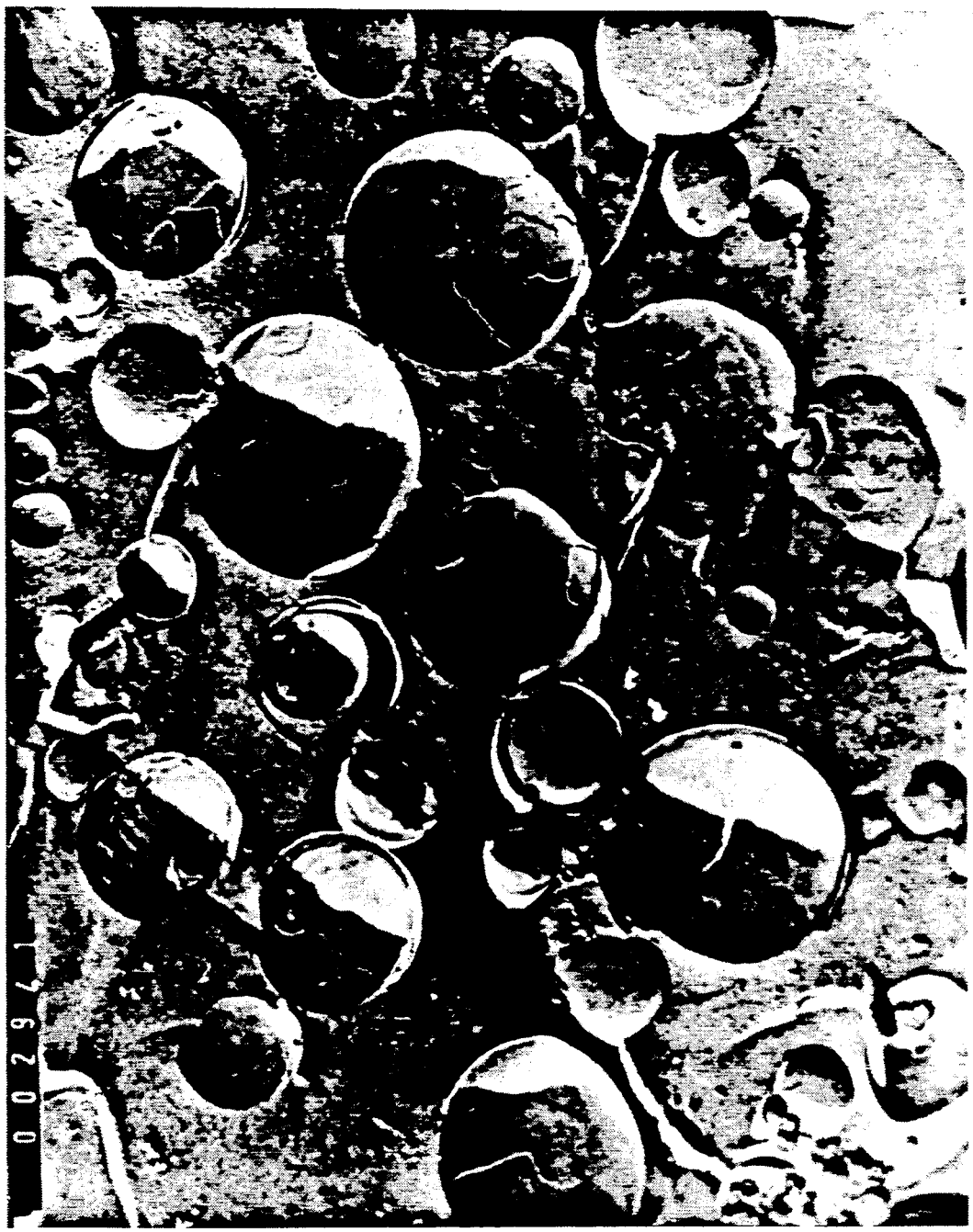
FIG. 4 is a freeze-fracture replicate of DMPC/Chol:-sucrose:water:BSA vesicles.

Freeze-fracture replicates of both egg PC:sodium chloride:$^{14}$C Inulin (FIG. 3) and DMPC/Chol:sucrose:water:BSA (FIG. 4) osmotically derived vesicles were produced and examined by electron microscopy. Egg PC:saline vesicles osmotically derived exhibit broad size distributions of aggregated multilamellar structures. DMPC/Chol:sucrose:water osmotically derived vesicles show oligolamellar structures with a limited size distribution in the range of 0.15 u to 0.75 u. The vesicles are spherical and exhibit varying interlamellar spacings, with fracture planes following lamellar contours and few cross fractures, indicative of swollen vesicles. There is no aggregation of vesicles.

From the above examples, it is apparent that the present process of producing osmotically derived vesicles is a viable system for solvent-free entrapment of solute in lipid vesicles. More specifically, the loading material in the above examples was added to the starting lipid materials only after the complete removal of solvent and rehydration of the liposomes. Thus, loading materials were at no time in contact with organic solvents, frozen or otherwise subjected to conditions that might adversely affect "process sensitive" active agents. Additionally, the preferred use of tangential flow filtration produces similarly sized vesicles substantially absent residual active agent in the solution. By employing a final filtration step using a molecular weight filter of 300,000 most active agents free in solution can be separated from liposomes entrapping those active agents.

TABLE 1

| Osmotic agent | mol. wt. (MW) | solubility limit in water* (mg/ml @ 298 deg. K) | molarity at solubility limit (m) | experimentally determined solution density at solubility limit (d) | molarity at solubility limit** (M) | osmotic pressure at solubility limit*** (atm) |
|---|---|---|---|---|---|---|
| sodium chloride | 58.4 | 357 | 6.113 | 1.208 | 5.442 | 265.96**** |
| D-b-glucose | 180.2 | 909 | 5.044 | 1.114 | 2.944 | 71.94 |
| D-sorbitol | 182.2 | 830 | 4.555 | 1.183 | 2.945 | 71.96 |
| D-mannitol | 182.2 | 181 | 0.993 | 1.06 | 0.891 | 21.77 |
| a-lactose H2O | 342.3 | 200 | 0.555 | 1.071 | 0.5 | 12.22 |
| sucrose | 342.3 | 2000 | 5.843 | 1.326 | 2.582 | 63.09 |
| glycine | 75.1 | 250 | 3.329 | 1.081 | 2.879 | 70.35 |
| TRIS | 121.1 | 290 | 2.395 | 1.059 | 1.966 | 48.04 |
| CHES | 207.3 | 175 | 0.844 | 1.047 | 0.752 | 18.38 |
| HEPES | 238.3 | 548 | 2.23 | 1.123 | 1.635 | 39.95 |

*The Merck Index, Tenth Edition - Merck & Co., Rahway, N.J. 1983
**$M = 1000 \times d \times m/1000 + (MW \times m)$
***$pl = MRT$
****assuming 100% dissociation to free ions

TABLE 2

| Lipid | osmotic agent | empty liposome process | osmotic agent concentration | loading material | OD vesicle process | % loading |
|---|---|---|---|---|---|---|
| EPC | NaCl | SPLV/CH2Cl2 | 228 mg/ml | 14C inulin | step dilution | 12.1* |
| DMPC | glucose | mod. SPLV | 1000 mg/ml | BSA | TFF/small vol. | 15.8 |
| EPC | glucose | mod. SPLV | 1000 mg/ml | BSA | TFF/small vol. | 24 |
| EPC | lactose | mod. SPLV | 100 mg/ml | BSA | TFF/small vol. | 11.9 |

*Samples used for freeze fracture and EM analysis

What is claimed is:

1. Method of producing liposome vesicles comprising active agent comprising contacting liposomes including an entrapped intralamellar osmotic agent one or more times with a washing solution including active agent wherein said solution is effectively hypotonic to said entrapped osmotic agent thereby causing the active agent to be encapsulated in the liposomes.

2. The method of claim 1 wherein said osmotic agent is a sugar or a salt.

3. The method of claim 1 wherein said active agent is a drug.

4. The method of claim 1 wherein said active agent is solvent sensitive.

5. The method of claim 1 wherein said active agent is process sensitive.

6. The method of claim 1 further comprising the contacting of the liposomes including intralamellar osmotic agent with the washing solution including active agent in discrete addition steps.

7. The method of claim 1 further comprising the contacting of the liposomes including intralamellar osmotic agent with the washing solution including active agent via linear osmotic gradient.

8. The method of claim 1 further comprising the contacting of the liposomes including intralamellar osmotic agent with the washing solution including active agent via tangential flow.

9. The method of claim 1 wherein the concentration of intralamellar osmotic agent in the intralamellar aqueous phase is from about 50 to about 2,500 mg/ml.

10. The method of claim 1 wherein the active agent is a protein or immunogen.

11. A method of producing liposome vesicles loaded with an active agent comprising the steps of:
(i) mixing lipid and osmotic agent in an organic solvent and removing the solvent and suspending the resulting material in an aqueous solution thus forming initial liposomes entrapping the osmotic agent;
(ii) combining the initial liposomes of step (i) with a washing solution of active agent which is effectively hypotonic to the entrapped osmotic agent of the initial liposomes;

the entrapped osmotic agent in the liposome and the washing solution including active agent each being present in relative concentrations such that the washing solution is effectively hypotonic so as to cause the liposomes to swell, rupture under osmotic pressure, release osmotic agent into the washing solution and re-form encapsulating active agent.

* * * * *

UNITED STATES PATENT AND TRADEMARK OFFICE
CERTIFICATE OF CORRECTION

PATENT NO. : 5,049,392

DATED : September 17, 1991

INVENTOR(S) : Alan L. Weiner, Frank G. Fielder

It is certified that error appears in the above-identified patent and that said Letters Patent is hereby corrected as shown below:

Column 7, line 29, delete "active" and insert therefor --osmotic--.

Claim 1, line 5, delete "thereby causing the active agent to be encapsulated in the liposomes" and insert therefor --thereby causing the liposomes to rupture and re-form encapsulating the active agent--.

Signed and Sealed this

Twenty-fourth Day of August, 1993

Attest:

BRUCE LEHMAN

*Attesting Officer*  *Commissioner of Patents and Trademarks*